United States Patent [19]

Wedemeyer et al.

[11] 4,326,080
[45] Apr. 20, 1982

[54] PROCESS FOR THE PREPARATION OF 4-AMINO-DIPHENYLAMINES

[75] Inventors: Karlfried Wedemeyer, Cologne; Siegfried Böhm, Dormagen, both of Fed. Rep. of Germany

[73] Assignee: Bayer Aktiengesellschaft, Leverkusen, Fed. Rep. of Germany

[21] Appl. No.: 158,540

[22] Filed: Jun. 11, 1980

[30] Foreign Application Priority Data

Jul. 3, 1979 [DE] Fed. Rep. of Germany ....... 2926714

[51] Int. Cl.³ .................... C07C 85/02; C07C 85/06
[52] U.S. Cl. .................................. 564/402; 564/403
[58] Field of Search ............................... 564/402, 403

[56] References Cited

U.S. PATENT DOCUMENTS

| 1,449,423 | 3/1923 | Lowy et al. | 564/402 |
| 3,384,667 | 5/1968 | Hamilton | 564/402 X |
| 3,860,650 | 1/1975 | Becker et al. | 564/403 X |
| 4,148,823 | 4/1979 | DuBois | 564/403 |
| 4,206,150 | 6/1980 | Slaugh | 564/402 X |

FOREIGN PATENT DOCUMENTS

| 1179775 | 5/1959 | France | 564/403 |
| 46-23052 | 1/1971 | Japan | 564/402 |
| 46-23053 | 1/1971 | Japan | 564/402 |
| 49-29176 | 1/1974 | Japan | 564/402 |
| 49-14737 | 10/1974 | Japan | 564/402 |
| 49-14738 | 10/1974 | Japan | 564/402 |
| 577901 | 6/1946 | United Kingdom | 564/402 |
| 611316 | 10/1948 | United Kingdom | 564/402 |

*Primary Examiner*—John Doll
*Attorney, Agent, or Firm*—Sprung, Felfe, Horn, Lynch & Kramer

[57] ABSTRACT

A process for the preparation of a 4-aminodiphenyl amino derivative which comprises:
(a) contacting a hydroxybenzene of the formula

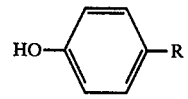

wherein R is hydroxyl or amino with an aniline compound of the formula

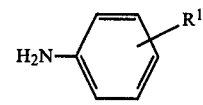

wherein $R_1$ represents hydrogen or an alkyl radical in the presence of a γ-aluminum oxide containing catalyst; and
(b) contacting the product from step (a) with ammonia in the presence of the same γ-aluminum oxide containing catalyst used in step (a).

10 Claims, No Drawings

PROCESS FOR THE PREPARATION OF 4-AMINO-DIPHENYLAMINES

The invention relates to a process for the preparation of 4-amino-diphenylamines.

Various possibilities of preparing 4-amino-diphenylamines industrially are known. Thus, according to U.S. Pat. No. 2,927,943 and U.S. Pat. No. 3,313,854, it is possible to react p-nitro-chloro-benzene with aniline in the presence of copper catalysts to give p-nitro-diphenylamine and to reduce this to give p-amino-diphenylamine. It is also possible, according to DE-OS (German Published Specification) No. 2,654,936, to nitrosate diphenylamine and to rearrange the resulting N-nitroso-diphenylamine in a medium containing hydrochloric acid to give p-nitroso-diphenylamine. Reduction of the nitroso group in p-nitroso-diphenylamine to the amino group can be carried out with sodium sulphide, according to DE-OS (German Published Specification) No. 2,355,737. In both process routes, at least stoichiometric amounts of inorganic salts which pollute the effluent are unavoidably formed.

The reaction of p-hydroxy-diphenylamine with ammonia in the presence of catalysts to give p-amino-diphenylamines is known from Canadian Patent No. 1,006,183. Catalysts which are mentioned are, for example, nickel, platinum and palladium. Before using these catalysts, it is necessary to activate them with hydrogen. The expensive safety measures arising when working with hydrogen must be taken during this activation. The catalysts used in this process, which are generally known as hydrogenation/dehydrogenation catalysts, are very sensitive systems which can easily be poisoned and thus decrease in activity (Ullmann, 1963, volume 14, page 643, Ann. 565, 51 (1948).

A process has been found for the preparation of 4-amino-diphenylamine derivatives, which is characterised in that hydroxybenzene derivatives of the formula

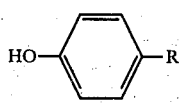
(I)

wherein

R denotes hydroxyl or amino, are reacted with an aniline derivative of the formula

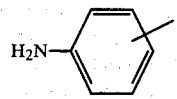
(II)

wherein $R^1$ represents hydrogen or an alkyl radical, in the presence of a catalyst containing $\gamma$-aluminum oxide, and the product is then treated with ammonia in the presence of the same catalyst.

A hydroxy-diphenylamine derivative of the formula

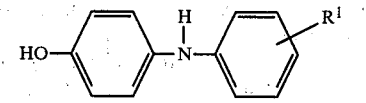
(III)

wherein $R^1$ has the abovementioned meaning, is formed as the intermediate product in the process according to the invention and is usually not isolated. However, it is, of course, also possible to isolate the hydroxy-diphenylamine derivative as an intermediate product and then to react it, according to the invention, with ammonia in the presence of a catalyst containing $\gamma$-aluminum oxide.

The process according to the invention can be illustrated by the following equations:

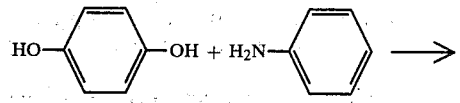

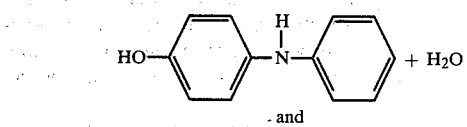

and

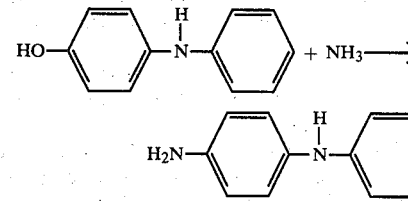

An alkyl radical ($R^1$) can be a straight-chain or branched aliphatic hydrocarbon radical with 1 to about 12 carbon atoms. A lower alkyl radical with up to about 6 carbon atoms is preferred. The following alkyl radicals may be mentioned as examples: methyl, ethyl, propyl, isopropyl, butyl, isobutyl, pentyl, isopentyl, hexyl and isohexyl.

Hydroxybenzene derivatives for the process according to the invention can be, for example, hydroquinone or p-aminophenol.

Hydroxybenzene derivatives are known (French Patent No. 1,079,454 and German Reichspatent No. 83,433 and they can be prepared, for example, by oxidation of p-diisopropylbenzene with cumene hydroperoxide (hydroquinone) or by rearrangement of phenylhydroxylamine with acids (p-aminophenol).

Aniline derivatives for the process according to the invention can be, for example, aniline, o-, m- or p-methylaniline, o-, m- or p-ethylaniline, o-, m- or p-propylaniline, o-, m- or p-isopropylaniline, o-, m- or p-butylaniline, o-, m- or p-isobutylaniline, o-, m- or p-pentylaniline, o-, m- or p-isopentylaniline, o-, m- or p-hexylaniline or o-, m- or p-isohexylaniline. Preferred aniline derivatives are aniline and o-, m- or p-methylaniline.

Aniline derivatives are in themselves known (BIOS Report No. 1157, page 25) and they can be prepared, for example, by reduction of nitrobenzene derivatives with iron fillings.

The process according to the invention is carried out in the presence of $\gamma$-aluminum oxide as a catalyst. $\gamma$-Aluminum oxide is in itself known (Ullmann, 1974, volume 7, page 298 et seq.) and can be prepared, for example, by calcining hydrated aluminum oxides at elevated temperature.

The γ-aluminum oxide catalyst can be doped with solid acid oxides, such as silicon dioxide, tungsten trioxide, chromium-III oxide and/or phosphorus pentoxide. A non-doped aluminum oxide is preferably used for the process according to the invention.

The amount of γ-aluminum oxide for the process according to the invention can vary within wide limits, and in general it is appropriate, in the case of a discontinuous procedure, to employ 0.1 to 10 parts by weight of γ-aluminum oxide per 1 part by weight of hydroxybenzene derivative. 0.5 to 5 parts by weight of γ-aluminum oxide are preferably employed per 1 part by weight of the hydroxybenzene derivative.

In the case of the discontinuous procedure, it is, of course, possible to use the catalyst several times. In the case of a continuous procedure, the catalyst is preferably located in a reaction tube and the reaction mixture is passed through.

The ratio of hydroxybenzene derivative to aniline derivative is essentially determined by the stoichiometry of the reaction. It is possible to employ the aniline component in excess and thus in practice to use it as the solvent.

In general, 1 to 10 mols of the aniline derivative can be employed per 1 mol of the hydroxybenzene derivative.

When hydroquinone is used, it is particularly preferable to employ 1.05 to 8 mols of the aniline derivative per 1 mol of hydroquinone.

When 4-aminophenol is used as the hydroxybenzene derivative, it is particularly preferable to employ 2 to 8 mols of the aniline derivative per 1 mol of 4-aminophenol.

The ratio of ammonia to hydroxybenzene derivative can be varied within wide limits. In general, ammonia is employed in excess, for example in an amount of 10 to 40 mols per 1 mol of the hydroxybenzene derivative.

When hydroquinone is used, it is preferable to employ, in the second reaction stage, 15 to 30 mols, particularly preferably 18 to 28 mols, of ammonia per 1 mol of hydroquinone.

When 4-aminophenol is used, it is preferable to employ 15 to 30 mols, particularly preferably 18 to 28 mols, of ammonia per 1 mol of 4-aminophenol.

The process according to the invention is in general carried out in the temperature range from 200° to 450° C.

The reaction of a dihydroxy-benzene derivative with an aniline derivative is preferably carried out in the temperature range from 200° to 350° C., particularly preferably from 220° to 300° C., and after adding the ammonia, the reaction temperature is increased up to the range from 300° to 450° C., preferably from 320° to 400° C.

When an aminobenzene derivative is used, the entire reaction is preferably carried out in the temperature range from 300° to 450° C., preferably from 320° to 400° C.

In a particularly preferred embodiment of the process according to the invention, 1 to 10 mols of aniline are reacted per mol of hydroquinone, in the temperature range from 230° to 280° C. Further reaction of the intermediate product with 15 to 30 mols of ammonia is carried out in the temperature range from 330° to 380° C. in this preferred embodiment.

In another preferred embodiment of the process according to the invention, 4-amino-phenol is reacted with aniline in the temperature range from 330° to 380° C. and the resulting mixture of 4-hydroxy- and 4-amino-diphenylamine is treated with 15 to 30 mols of ammonia in the same temperature range.

The process according to the invention is in general carried out under increased pressure. It can appropriately be carried out in the pressure range from 1 to 400 bars. The pressure range from 10 to 350 bars is preferred for the process according to the invention.

The reaction is preferably carried out in an autoclave, especially in the case of a discontinuous procedure for the process according to the invention. The pressure which is established in the closed autoclave at the chosen reaction temperature is appropriately chosen as the reaction pressure.

The process according to the invention can be carried out in the presence of solvents which do not react with the reaction components. However, it is in general preferable to carry out that process according to the invention in an excess of the aniline component.

The process according to the invention is in general carried out as a one-pot process, without isolating the hydroxy-diphenylamine derivative of the formula (III) as an intermediate product. However, if the intermediate product has been isolated or if it is desired to react a hydroxy-diphenylamine derivative of the formula (III) which has been prepared in another manner, the procedure followed can, of course, be that according to the invention.

In the case of a discontinuous procedure, for example, the reaction components and the catalyst can be stirred in an autoclave at the particular reaction temperature. Advantageously, the hydroxybenzene derivative is initially stirred with the catalyst and the aniline derivative at the reaction temperature of the first reaction step, ammonia is then pumped in and the mixture is warmed to the reaction temperature of the second reaction step. After cooling the autoclave, the reaction product is separated off from the catalyst in a manner which is in itself known, for example by filtration, and purified by distillation.

In the case of a continuous procedure, for example, the hydroxybenzene derivative can be dissolved in the aniline derivative and the solution can be passed through a tube which is filled with γ-aluminum oxide catalyst and has been warmed to the particular reaction temperature. The reaction can be carried out either in the vapour phase or in the liquid phase. The hydroxybenzene/aniline derivative mixture can be passed through the reaction tube either from the top downwards or from the bottom upwards. The reaction with the ammonia can be carried out in a similar manner, the example by pumping the 4-hydroxydiphenylamine obtained as the intermediate product through the reaction tower described above and metering ammonia into the product before entry into the contact zone heated to the particular reaction temperature. The crude product issuing from the reaction tower is let down and cooled, and worked up by distillation.

In a particularly preferred embodiment, however, the process is carried out in two reaction towers connected in series. The reaction of the hydroxybenzene derivative with the aniline derivative is carried out in the first reaction tower and the mixture of 4-hydroxy-diphenylamine and, if appropriate, aniline, issuing from this tower is forced into the second reaction tower, connected downstream, without intermediate isolation. Before entry into the second reaction tower, the ammonia is metered in such that 4-hydroxy-diphenylamine, aniline and ammonia flow through the γ-aluminum oxide catalyst in co-current. The reaction temperature of the first reactor is preferably 230° to 280° C. and that of the second reactor is preferably 330° to 380° C. The pressure in the reactors can vary within wide limits, depending on the nature of the reactants and the molar ratio. If appropriate, it can be increased further, for example by adding an inert gas.

A reaction product which can be worked up directly by distillation is obtained by the process according to the invention. No inorganic constituents are obtained during working up; any residues which may be obtained can be burned, if appropriate, without pollution of the environment. A solvent optionally used can be recovered and re-used. 4-Amino-diphenylamine derivatives of the formula

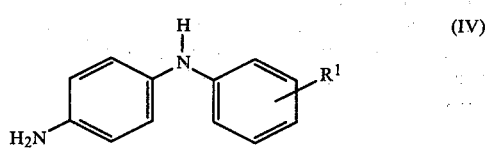

(IV)

wherein $R^1$ has the abovementioned meaning, are obtained by the process according to the invention.

It was not to be expected that 4-amino-diphenylamine derivatives are formed by the process according to the invention. The process according to the invention is surprising, since it was known that reaction of hydroquinone with ammonia on a catalyst containing γ-aluminum oxide leads to phenylenediamine and not to the corresponding 4-aminophenol (Japanese No. 46/23,053, Japanese No. 49/14,737 and japanese No. 49/29,176). Similarly, amination of hydroquinone with aniline on molybdenum oxide or nickel oxide on aluminum oxide/silicon dioxide supports leads to N,N'-diphenyl-1,4-diaminobenzene and not to 4-hydroxy-diphenylamine (U.S. Pat. No. 3,510,518).

The 4-amino-diphenylamine derivatives are advantageously obtained, in high yields and with high selectivity, by the process according to the invention. No pollution of the environment by by-products occurs.

Amino-diphenylamines can be used as intermediate products for the preparation of bis-(4-anilino-phenoxy) esters, which are employed, for example, as antiaging agents in polymeric compounds (DE-OS (German Published Specification) No. 2,748,205, DE-OS (German Published Specification) No. 2,753,194 and DE-OS (German Published Specification) No. 2,801,414).

EXAMPLE 1

396 g (3.6 mols) of hydroquinone are dissolved in 1,338 g (14.4 mols) of aniline in a calibrated measuring vessel. This solution is pumped, via a steel line and at a rate of 66 g of hydroquinone (0.6 mol/hour) and 223 g of aniline (2.4 mols/hour), into a steel reactor which has been warmed to 270° C., has a height of 160 cm and an internal diameter of 2.5 cm and is filled with 800 ml of γ-Al₂O₃ lumps 1 cm in diameter and 1 cm long. An electrically heated pre-warming zone is connected upstream of the reactor. The reaction mixture is under a pressure of 20 bars. The reaction product issuing from the valve is condensed in a steel condenser charged with silicone oil and is collected in a stock vessel. From the stock vessel, it is pumped from a constant level into a second tube, heated to 350° C., with the same dimensions and packing. 194 g/hour (12 mols) of ammonia are metered into the mixture using a high-pressure pump. The pressure at the top of the reactor is adjusted to 250 bars. The reaction mixture issuing from the valve is cooled, condensed and collected in a 2.5 l receiver. The ammonia is passed into an overflow vessel filled with water and is not isolated.

Reaction product isolated per hour: 277 g.

The excess aniline is distilled off under 20 mbars. 110 g of a residue with a content of 4-amino-diphenylamine of 86.5 g (78.6 mol %), relative to hydroquinone employed.

Yield: 78.6% of theory, relative to hydroquinone employed.

EXAMPLE 2

27 g (0.25 mol) of hydroquinone, 186 g (2.0 mols) of aniline and 81 g of γ-Al₂O₃ catalyst DC-10 are initially introduced into a 0.7 l steel autoclave. The autoclave is flushed with nitrogen and the mixture is stirred at 270° C. for 2 hours (pressure: about 20 bars). After cooling the mixture to room temperature, 85 g (5.0 mols) of ammonia are forced into the autoclave and the mixture is stirred at 350° C. for 6 hours. A pressure of 250 to 300 bars is established.

Five of these batches are combined, the catalyst is filtered off from the liquid constituents and the residue on the filter is separated off three times with 1 l of dimethylformamide at 50° C. for 1 hour. The organic filtrates are combined and concentrated. 1,098 g of crude solution remain.

From the solution remaining amounts of aniline and dimethylformamide are distilled off under 20 mbars and at bottom temperature of 150° C., up to an overhead temperature of 150° C. The residue is then distilled under nitrogen, under a high vacuum of 0.5 mbar, up to a bottom temperature of 300° C.

204.5 g (boiling point up to 200° C.) of distillate which solidifies in the receiver, =(88.9 mol %) and 9.6 g =(4.2) % by weight of residue, relative to the theoretical yield of 4-aminodiphenylamine of 230 g (1.25 mols), relative to hydroquinone employed, are obtained. The purity, relative to 4-aminodiphenylamine, is 88.1%. It follows that the yield is 78.3% of the theoretical yield.

EXAMPLES 3 TO 5

Examples 3 to 6 were carried out analogously to Example 2, except that doped γ-Al₂O₃ of the composition indicated was used instead of pure γ-Al₂O₃:

| Example | Catalyst | Yield, mol % of 4-amino-diphenylamine |
|---|---|---|
| 3 | γ-Al₂O₃/WO₃/P₂O₅ | 69.3 |
| 4 | γ-Al₂O₃/MoO₃ | 63.0 |
| 5 | γ-Al₂O₃/SiO₂ | 49.3 |

EXAMPLE 6

108 g (about 1.0 mol) of hydroquinone, 108 g of comminuted γ-aluminum oxide catalyst and 186 g (2.0 mols) of aniline are stirred at 270° C. in a nitrogen atmosphere in a 700 ml steel autoclave for 4 hours. The pressure is 20 bars. The light-coloured, solid reaction product is extracted with methylene chloride in a Soxleth extractor for 16 hours. The filtrate is distilled under an oil pump vacuum.

| First runnings: | 84 g | Boiling point$_{2.7\text{ mbar}}$ → 167° bottom |
| --- | --- | --- |
| | | → 71° top |
| Main runnings: | 166 g | Boiling point$_{1.7\text{ mbar}}$ → 300° bottom |
| | | → 203° top |
| Residue: | 6 g | |
| | 256 g | |

Analysis of the distillate: 94.7% of 4-hydroxydiphenylamine.

This gives a yield of 4-hydroxydiphenylamine of 85.0% of the theoretical yield.

EXAMPLE 7

108 g (about 1.0 mol) of hydroquinone, 108 g of γ-aluminum oxide catalyst and 215 g (2.0 mols) of o-toluidine are stirred at 270° C. in a nitrogen atmosphere in a 700 ml steel autoclave for 3 hours. The pressure is 6 bars. The mixture is worked up analogously to Example 7.

| Distillate: | 170 g = (85.9%) | Melting point: 84–88° |
| --- | --- | --- |
| | | Boiling point$_{1.3}$ rising to 215° C. |
| Distillation residue: | 12 g = (6.1%) | |
| Residue in the catalyst: | 10 g = (5.1%) | |
| | 192 g = (97.5%) | |

Analysis of the distillate: 95.3% = (81.8 mol %) of 4-hydroxy-2′-methyldiphenylamine.

EXAMPLE 8

108 g (about 1.0 mol) of hydroquinone, 108 g of γ-aluminum oxide catalyst and 215 g (about 2.0 mols) of m-toluidine are stirred at 270° C. under nitrogen in a 700 ml steel autoclave for 3 hours. The pressure is 19.1 bars. The reaction mixture is worked up analogously to Example 7.

| Distillate: | 172.5 g = (87.1%) | Melting point: 88–92° |
| --- | --- | --- |
| | | Boiling point$_{0.7}$: 235° |
| Distillation residue: | 12.0 g = (6.1%) | |
| Residue in the catalyst: | 9.5 g = (4.6%) | |
| | 194.0 g = (98.3%) | |
| Theoretical: | 197.0 g = (100%) | |

Analysis of the distillate: 95.3% of 4-hydroxy-3′-methyldiphenylamine. Yield: 83.0% (of the theoretical yield)

EXAMPLE 9

108 g (about 1.0 mol) of hydroquinone, 215 g (about 2.0 mols) of p-toluidine and 108 g of γ-aluminum oxide catalyst are stirred at 270° C. under nitrogen in a 700 ml steel autoclave for 4 hours. The pressure is 19 bars. The reaction mixture is worked up analogously to Example 7.

| Distillate: | 266 g (contains p-toluidine) |
| --- | --- |
| Distillation residue: | 18 g = (9.1%) |
| Residue in the catalyst: | 8 g = (4.1%) |
| Analysis of the distillate: | 34.2% of p-toluidine, and 60.6% of 4-hydroxy-4′-methyldiphenylamine |
| Yield: | 81.4% (of the theoretical yield) |

Melting point: 120°–122°, after recrystallisation from toluene.

EXAMPLE 10

45 g (about 0.24 mol) of 4-hydroxydiphenylamine, 88 g of γ-aluminum oxide catalyst and 120 g (7.0 mols) of NH$_3$ are stirred at 350° C. under nitrogen in a 700 ml steel autoclave for 2 hours. A pressure of 395 bars is established. A total of 8 experiments are carried out. The pressure is 350 to 395 bars. Each experimental batch is extracted with dimethylformamide. The combined dimethylformamide solutions are distilled under nitrogen. The major proportion of the reaction product distils at 174° to 177° C. under 2.0 mbars. The overhead temperature increases to 210° C. towards the end of the distillation.

| Distillate: | 305 g = (85.2%) |
| --- | --- |
| Distillation residue: | 21 g = (5.9%) |
| Analysis after distillation: | 96.4% of 4-aminodiphenylamine |
| Yield | 82.1% (of the theoretical yield). |

EXAMPLE 11

4-Hydroxy-2′-methyl-, 4-hydroxy-3′-methyl- and 4-hydroxy-4′-methyl-diphenylamine are reacted with ammonia at 350° C. under nitrogen in the course of 2 hours in the same manner as in Example 11.

4-Amino-2′-methyldiphenylamine

Pressure: 272 bars
Ammonia: 85 g=(5.0 mols)
Yield of 4-amino-2′-methyldiphenylamine: 70.7% of the theoretical yield.

EXAMPLE 12

4-Amino-3′-methyldiphenylamine

Pressure: 260 bars
Ammonia: 85 g=(5.0 mols)
Yield of 4-amino-3′-methyldiphenylamine: 86.1% of the theoretical yield.

EXAMPLE 13

4-Amino-4′-methyldiphenylamine

Pressure: 250 bars
Ammonia: 85 g=(5.0 mols)
Yield of 4-amino-4′-methyldiphenylamine: 82.2% (of the theoretical yield)

EXAMPLE 15

27 g (0.25 mol) of 4-aminophenol, 54 g of γ-Al$_2$O$_3$ catalyst and 186 g (2.0 mols) of aniline are stirred at 350° C. under nitrogen in a 0.7 l steel autoclave for 3 hours. The pressure is 20 bars. The mixture is cooled, 120 g (about 7.0 mols) of ammonia are forced into the autoclave and the mixture is stirred at 350° C. for a further 4 hours. The dark smeary residue is stirred with 2 l of DMF under nitrogen at room temperature, the catalyst is filtered off and the filtrate is investigated by gas chromatography.

Yield: 29.3% (of the theoretical yield).

EXAMPLES 15 AND 16

Experiments 16 and 17 were carried out in an analogous manner to Example 15, except that the particular doped catalyst containing $\gamma$-$Al_2O_3$ was used instead of pure $\gamma$-$Al_2O_3$.

| Example | Catalyst | Yield (relative to the 4-aminophenol employed): mol % of 4-aminodiphenylamine |
|---------|----------|-----|
| 15 | $\gamma$-$Al_2O_3$/$MoO_3$ | 27.8 |
| 16 | $\gamma$-$Al_2O_3$/$WO_3$/$P_2O_5$ | 37.2 |

What is claimed is:

1. A process for the preparation of a 4-amino-diphenyl amino derivative which comprises:
(a) contacting a hydroxybenzene of the formula

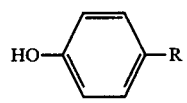

wherein R is hydroxyl or amino with an aniline compound of the formula

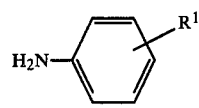

wherein $R_1$ represents hydrogen or an alkyl radical in the presence of a $\gamma$-aluminum oxide containing catalyst; and
(b) contacting the product from step (a) with ammonia in the presence of the same $\gamma$-aluminum oxide containing catalyst used in step (a).

2. A process according to claim 1, wherein undoped $\gamma$-aluminum oxide containing catalysts is employed in at least one step (a) or (b).

3. A process according to claim 1, wherein the reactions are conducted at a temperature of 200° C. to 450° C.

4. A process according to claim 1, wherein the process is conducted at a pressure in the range of 1 to 400 bars.

5. A process according to claim 1, wherein hydroquinone is reacted with 1 to 10 mols of said aniline derivative at a temperature in the range of 230° C. to 280° C. and the resultant reaction mixture is treated with 15 to 30 mols of ammonia at a temperature in the range of 330° C. to 380° C. in the presence of the same catalyst for both steps.

6. A process according to claim 1, wherein 4-aminophenol is reacted with aniline at a temperature in the range of from 330° C. to 380° C. and the resulting mixture of 4-hydroxy and 4-amino diphenylamine is treated with 15 to 30 mols of ammonia at a temperature in the range of from 330° to 380° C. in the presence of the same catalyst for both steps.

7. A process according to claim 1, wherein said aniline derivative is employed in a stoichiometric excess and said aniline derivative is a solvent for said hydroxy benzene derivative.

8. A process according to claim 1, wherein the process is conducted without isolation of the product of step (a) prior to contacting the product of step (a) with ammonia in accordance with step (b).

9. A process according to claim 8, wherein the process is conducted as a "one-pot" process without isolating the hydroxy-diphenyl amine intermediate.

10. A process according to claim 8, wherein the process is carried out in two reaction towers connected in series, the reaction of the hydroxybenzene derivative with the aniline derivative being carried out in a first reaction tower and the mixture of 4-hydroxy-diphenylamine and aniline derivative issuing from the first tower being forced into the second reaction tower, connected downstream, without isolation of the intermediate formed in the first tower and before entry of the same into the second reaction tower ammonia is metered in such that the flow of reaction product of step (a), unreacted aniline derivative and ammonia through the $\gamma$-aluminum oxide containing catalyst is co-current.

* * * * *